US00PP32523P2

(12) United States Plant Patent
Hartman

(10) Patent No.: US PP32,523 P2
(45) Date of Patent: Nov. 24, 2020

(54) ***CALADIUM* PLANT NAMED 'MOL 158-47'**

(50) Latin Name: ***Caladium* X *hortulanum***
Varietal Denomination: MOL 158-47

(71) Applicant: Robert Dale Hartman, Lake Placid, FL (US)

(72) Inventor: Robert Dale Hartman, Lake Placid, FL (US)

( * ) Notice: Subject to any disclaimer, the term of this patent is extended or adjusted under 35 U.S.C. 154(b) by 0 days.

(21) Appl. No.: 16/873,504

(22) Filed: Apr. 23, 2020

(51) Int. Cl.
*A01H 5/12* (2018.01)
*A01H 6/10* (2018.01)

(52) U.S. Cl.
USPC ..... Plt./373

(58) Field of Classification Search
USPC ..... Plt./373
See application file for complete search history.

*Primary Examiner* — Susan McCormick Ewoldt
*Assistant Examiner* — Karen M Redden
(74) *Attorney, Agent, or Firm* — C. A. Whealy

(57) ABSTRACT

A new and distinct cultivar of *Caladium* plant named 'MOL 158-47', characterized by its upright plant habit; intermediate height; dense and bushy appearance; vigorous growth habit and rapid growth rate; fancy-type leaves that are white and greenish white in color with a narrow dark green-colored leaf margin and greyed green or green-colored venation; and petioles that are tannish brown in color.

5 Drawing Sheets

Figure 1:
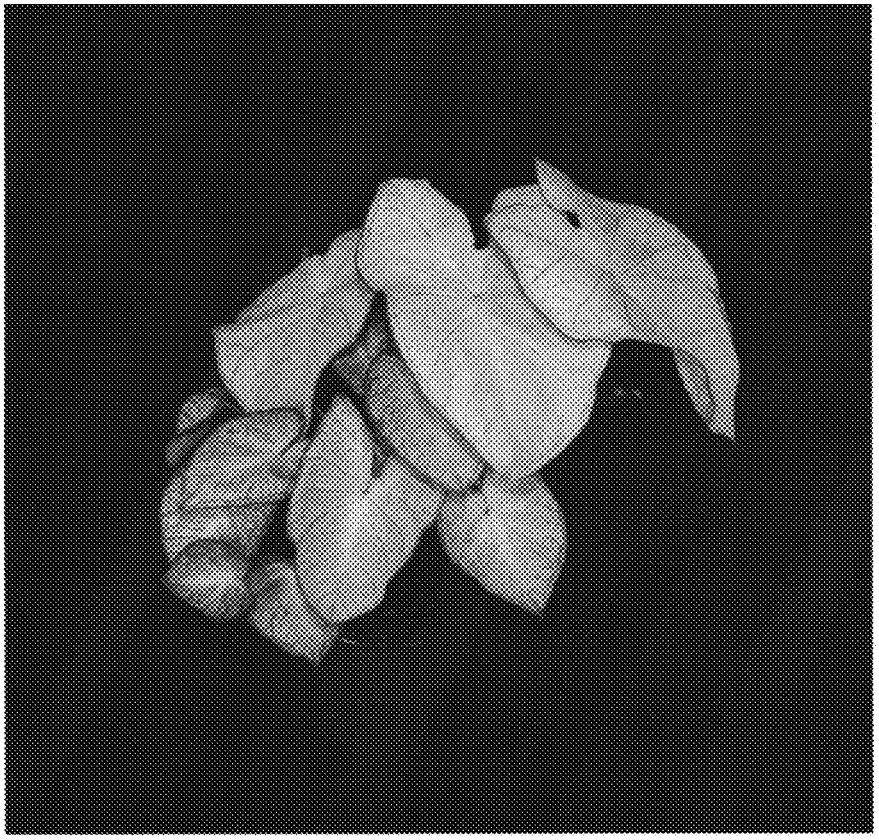

Botanical designation: *Caladium* X *hortulanum*.
Cultivar denomination: 'MOL 158-47'.

BACKGROUND OF THE INVENTION

The present invention relates to a new and distinct cultivar of *Caladium* plant, botanically known as *Caladium* X *hortulanum*, commercially referred to as a fancy leaf-type *Caladium* and hereinafter referred to by the name 'MOL 158-47'.

The objective of the Inventor's breeding program is to create new *Caladium* plants that have uniform plant habit, exceptional container and garden performance and attractive and unique leaf coloration.

The new *Caladium* plant originated from a cross-pollination made by the Inventor in April, 2009 in Avon Park, Fla. of *Caladium* X *hortulanum* 'Candidum Senior', not patented, as the female, or seed, parent with *Caladium* X *hortulanum* 'Aaron', not patented, as the male, or pollen, parent. The new *Caladium* plant was discovered and selected by the Inventor as a single plant within the progeny of the stated cross-pollination in a controlled outdoor nursery environment in Avon Park, Fla. in September, 2010.

Asexual reproduction of the new *Caladium* plant by "chipping" the tubers (cutting the tuber into segments with each segment containing an axillary bud and tuber cortical tissue) in a controlled outdoor nursery environment in Zolfo Springs, Fla. since April, 2011 has shown that the unique features of this new *Caladium* plant are stable and reproduced true to type in successive generations of asexual reproduction.

SUMMARY OF THE INVENTION

Plants of the new *Caladium* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'MOL 158-47'. These characteristics in combination distinguish 'MOL 158-47' as a new and distinct *Caladium* plant:

1. Intermediate in height and upright plant habit; dense and bushy appearance.
2. Vigorous growth habit and rapid growth rate.
3. Fancy-type leaves that are white and greenish white in color with a narrow dark green-colored leaf margin and greyed green or green-colored venation.
4. Petioles that are tannish brown in color.

Plants of the new *Caladium* differ primarily from plants of the female parent, 'Candidum Senior', in the following characteristics:

1. Plants of the new *Caladium* and 'Candidum Senior' differ in leaf color as leaves of the new *Caladium* are white and greenish white in color with a narrow dark green-colored leaf margin and greyed green or green-colored venation whereas leaves of 'Candidum Senior' are greenish white in color with medium green-colored venation and thin green-colored margins.
2. Plants of the new *Caladium* and 'Candidum Senior' differ in leaf petiole color as leaf petioles of the new *Caladium* are tannish brown in color whereas leaf petioles of 'Candidum Senior' are green in color with black-colored streaks.

Plants of the new *Caladium* differ primarily from plants of the male parent, 'Aaron', in the following characteristics:

1. Plants of the new *Caladium* and 'Aaron' differ in leaf color as leaves of the new *Caladium* are white and greenish white in color with a narrow dark green-colored leaf margin and greyed green or green-colored venation whereas leaves of 'Aaron' have white-colored venation and radiating interveinal areas surrounded with green-colored borders.

2. Plants of the new *Caladium* and 'Aaron' differ in leaf petiole color as leaf petioles of the new *Caladium* are tannish brown in color whereas leaf petioles of 'Aaron' are green in color.

Plants of the new *Caladium* can be compared to plants of *Caladium* X *hortulanum* 'Florida Moonlight', disclosed in U.S. Plant Pat. No. 14,565. In side-by-side comparisons, plants of the new *Caladium* differ primarily from plants of 'Florida Moonlight' in the following characteristics:

1. Plants of the new *Caladium* and 'Florida Moonlight' differ in leaf color as leaves of the new *Caladium* are white and greenish white in color with a narrow dark green-colored leaf margin and greyed green or green-colored venation whereas leaves of 'Florida Moonlight' have greenish white-colored leaves and venation.
2. Leaves of plants of the new *Caladium* are more rugose than leaves of plants of 'Florida Moonlight'.
3. Plants of the new *Caladium* and 'Florida Moonlight' differ in leaf petiole color as leaf petioles of the new *Caladium* are tannish brown in color whereas leaf petioles of 'Florida Moonlight' are more brown in color.
4. Plants of the new *Caladium* are more tolerant to *Xanthomonas* Leaf Spot than plants of 'Florida Moonlight'.

Plants of the new *Caladium* can also be compared to plants of *Caladium* X *hortulanum* 'White Cap', disclosed in U.S. Plant Pat. No. 23,815. In side-by-side comparisons, plants of the new *Caladium* differ primarily from plants of 'White Cap' in the following characteristics:

1. Plants of the new *Caladium* are shorter than and more mounding than plants of 'White Cap'.
2. Plants of the new *Caladium* and 'White Cap' differ in leaf color as leaves of the new *Caladium* are white and greenish white in color with a narrow dark green-colored leaf margin and greyed green or green-colored venation whereas leaves of 'White Cap' have white-colored venation and white, greyed green and green speckled interveinal areas and dark green-colored margins.
3. Plants of the new *Caladium* and 'White Cap' differ in leaf petiole color as leaf petioles of the new *Caladium* are tannish brown in color whereas leaf petioles of 'White Cap' are almost black in color with tannish green-colored stripes.

BRIEF DESCRIPTION OF THE PHOTOGRAPHS

The accompanying photographs illustrate the overall appearance of the new *Caladium* plant showing the colors as true as it is reasonably possible to obtain in colored reproductions of this type. Colors in the photographs may differ slightly from the color values cited in the detailed botanical description which accurately describe the colors of the new *Caladium* plant.

The photograph on the first sheet (FIG. 1 of 7) is a side perspective view of a typical plant of 'MOL 158-47' in a container and grown in a shade house (tuber de-eyed).

Figure 2:
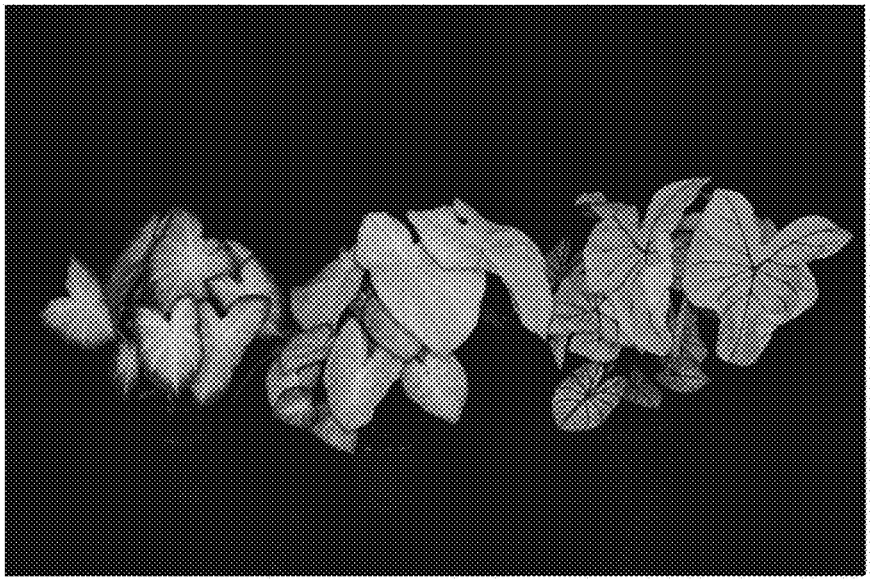

The photograph at the top of the second sheet (FIG. 2 of 7) is a comparison view of typical potted plants of the male parent, 'Aaron' (left), 'MOL 158-47' (center) and the female parent, 'Candidum Senior' (right).

Figure 3:
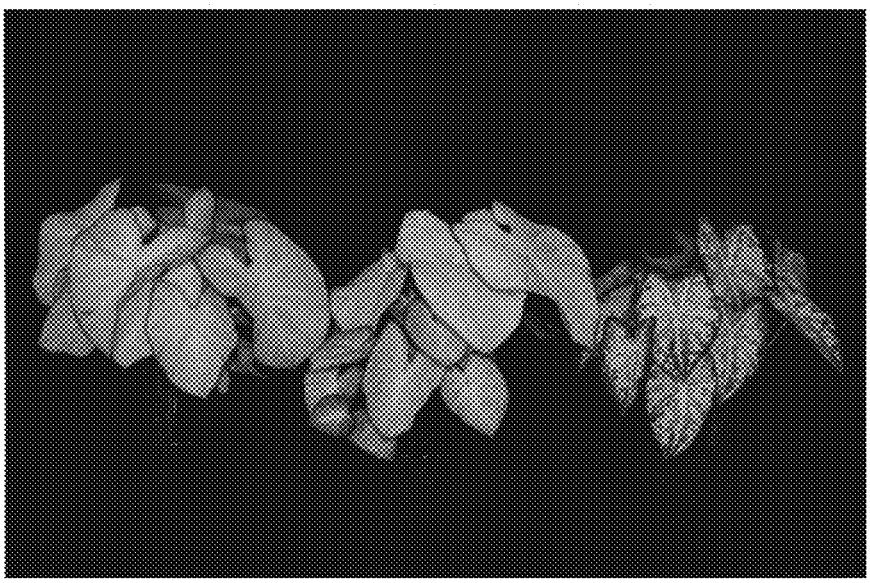

The photograph at the bottom of the second sheet (FIG. 3 of 7) is a comparison view of typical potted plants of 'Florida Moonlight' (left), 'MOL 158-47' (center) and 'White Cap' (right).

Figure 4:
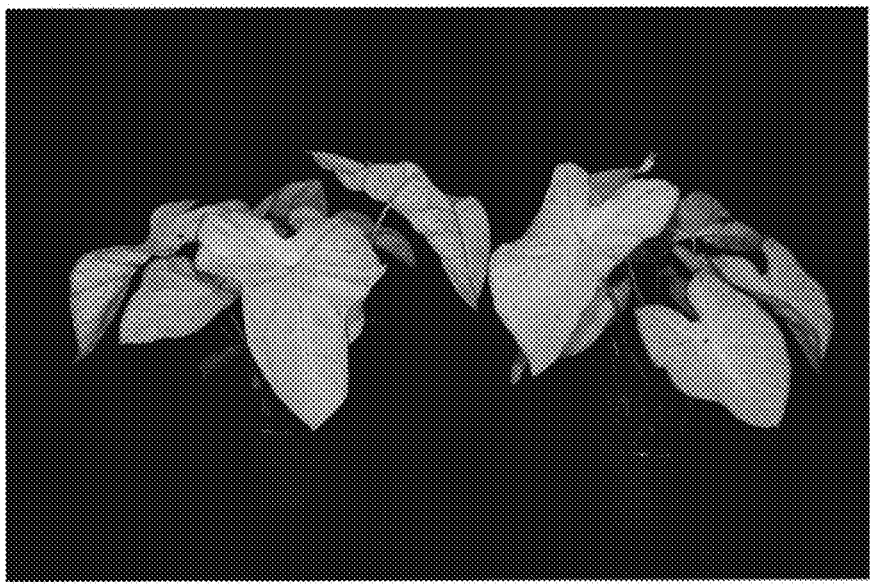

The photograph at the top of the third sheet (FIG. 4 of 7) is a comparison view of typical plants of 'MOL 158-47' grown in containers, the plant on the left has not had its tuber de-eyed and the plant on the right has had its tuber de-eyed prior to planting.

Figure 5:
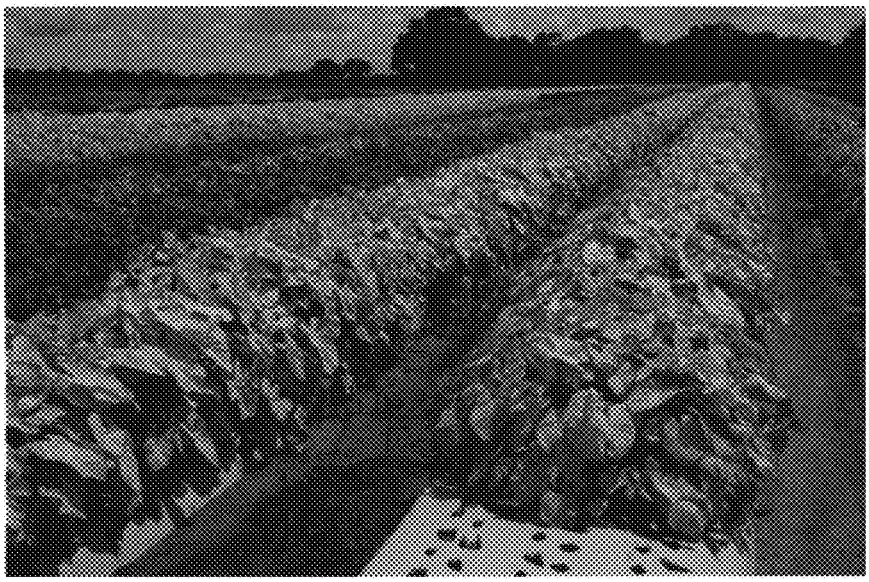

The photograph at the bottom of the third sheet (FIG. 5 of 7) is a side perspective view of typical plants of 'MOL 158-47' grown in an open production field.

Figure 6:
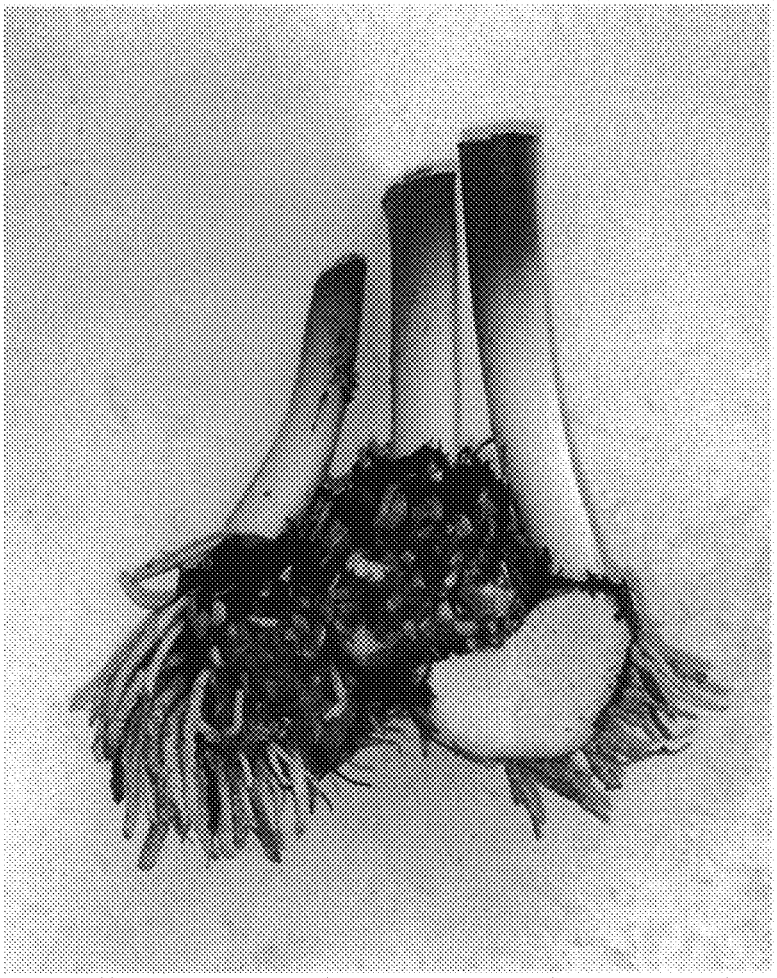

The photograph on the fourth sheet (FIG. 6 of 7) is a close-up view of typical freshly-harvested tubers with roots and leaf petioles of 'MOL 158-47'.

Figure 7:
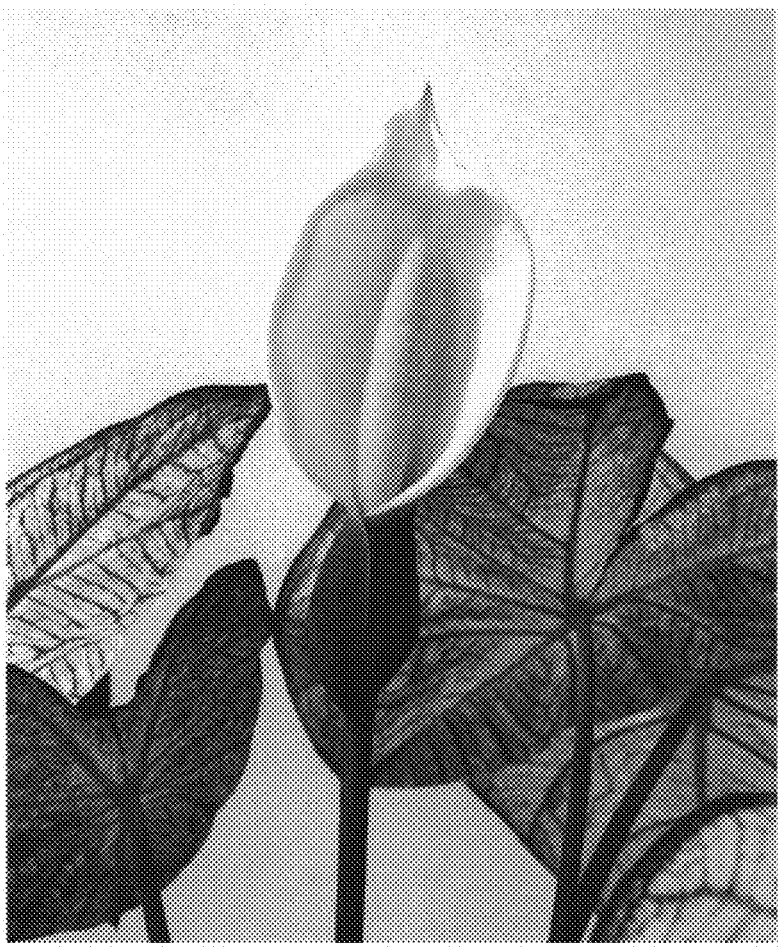

The photograph on the fifth sheet (FIG. 7. of 7) is a close-up view of a typical inflorescence of 'MOL 158-47'.

DETAILED BOTANICAL DESCRIPTION

The aforementioned photographs and following observations and measurements describe plants grown in 15-cm containers in a polypropylene-covered shade house (30% light reduction) in Avon Park, Fla. and plants grown in ground beds under full sunlight conditions in an outdoor nursery in Crewsville, Fla. The plants were grown under cultural practices typical of commercial shade house and outdoor nursery production. During the production of the shade house-grown plants, day temperatures ranged from about 28° C. to 33° C., night temperatures ranged from about 22° C. to 25° C. and light levels were about 8,000 foot-candles. During the production of the outdoor nursery-grown plants, day temperatures ranged from about 29° C. to 35° C., night temperatures ranged from about 23° C. to 26° C. and light levels ranged from 10,000 to 12,000 foot-candles. Plants grown in the shade house were five weeks old and plants grown in the outdoor nursery were six months old when the photographs and the detailed description were taken. In the following description, color references are made to The Royal Horticultural Society Colour Chart, 2015 Edition, except where general terms of ordinary dictionary significance are used.

Botanical classification: *Caladium* X *hortulanum* 'MOL 158-47'.

Parentage:

*Female, or seed, parent.*—*Caladium* X *hortulanum* 'Candidum Senior', not patented.

*Male, or pollen, parent.*—*Caladium* X *hortulanum* 'Aaron', not patented.

Propagation:

*Type.*—By "chipping" the tubers.

*Time to initiate roots, summer.*—About seven to ten days at temperatures about 32° C.

*Time to initiate roots, winter.*—About two to three weeks at temperatures about 24° C.

*Tuber description* (*outdoor nursery-grown plants*).—Appearance: Multi-segmented; individual segments irregular to elliptic in shape. Height: About 4.5 cm. Diameter: About 4.5 cm to 6.9 cm. Segment height: About 1.8 cm to 2.8 cm. Segment diameter: About 1.2 cm to 2.2 cm. Axillary bud shape: Roughly triangular. Axillary bud size: About 3 mm by 3.5 mm. Texture: Thick, starchy; somewhat brittle. Color: Periderm, freshly-harvested: Close to 199D. Periderm, dried: Close to 200A. Epidermis: Initially, close to N155C becoming closer to N155B to N155C with development. Cortical tissue: Close to 155A and N155D. Axillary buds: Close to 49D. Root description: Moderately thick, fleshy contractile roots with few lateral branches; color, close to N155D occasionally tinged with 181D. Rooting habit: Dense.

Plant description:

*Plant type*.—Herbaceous perennial; suitable as a potted plant in containers 15-cm to 25-cm and suitable as a landscape plant in shaded areas.

*Plant and growth habit*.—Intermediate in height and upright plant habit; dense and bushy appearance; vigorous growth habit and rapid growth rate; potted plants finish in saleable form in about five to six weeks after planting tubers; leaf petioles and leaves arise from one or more growing points on tubers; leaf petioles initially upright and somewhat outwardly leaning with development.

*Plant height, from soil level to top of foliar plane, shade house-grown potted plants*.—About 35 cm to 40 cm.

*Plant height, from soil level to top of inflorescences, shade house-grown potted plants*.—About 32.5 cm.

*Plant diameter or spread, shade house-grown potted plants*.—About 42 cm to 46 cm.

*Number of shoots per plant, shade house-grown potted plants, tubers not de-eyed*.—About two to three develop per #1 tuber.

*Number of shoots per plant, shade house-grown potted plants, tubers de-eyed*.—About three to four develop per #1 tuber.

*Cataphylls, shade house-grown potted plants*.—Length: About 8.2 cm to 9.4 cm. Width: About 1.2 cm to 2.2 cm. Shape: Linear or narrowly elliptic. Apex: Acute or obtuse. Base: Sheathing the stem. Color, outer surface: Initially close to 177D and 182D with stippling and streaks, close to 200C; with development, color becoming closer to 177B and 200C to 200D. Color, inner surface: Close to N155C; colors and patterns on outer surface visible on inner surface.

Leaf description:

*Arrangement and type*.—Alternate; simple; fancy-type.

*Length, shade house-grown potted plants*.—About 21.5 cm to 28.2 cm.

*Width, shade house-grown potted plants*.—About 15.2 cm to 19 cm; when flattened, about 15.5 cm to 20.5 cm.

*Shape*.—Ovate.

*Apex*.—Acute to acuminate.

*Base*.—Sagittate-peltate, cordate.

*Margin*.—Entire; mostly flat with broad undulations.

*Texture and luster, upper surface*.—Glabrous, interveinal areas may be slightly convex and concave; leathery; dull sheen.

*Texture and luster, lower surface*.—Smooth, glabrous; leathery; dull sheen and veins, slightly glaucous.

*Venation pattern*.—Pinnate.

*Color, shade house-grown potted plants*.—Developing leaves, upper surface: Background color: Close to 194C, 194D and N155D. Towards the margins: Close to 137B. Leaf edge: Narrow, close to 187A. Basal notch: Close to 187C. Leaf attachment point: Typically, close to N186D and 187C. Midvein: Proximally, close to 193B with streaks, close to 138C; distally, close to 193A with flecks, close to NN137B to NN137C; midvein surrounded by close to NN155D. Lateral venation: Close to 193B tinged with close to 138A to 138B and surrounded by close to NN155D; smaller veins, close to 137A. Interveinal areas: Close to 194C, 194D and N155D. Developing leaves, lower surface: Background color: Close to 147D. Towards the margins: Close to 191A. Leaf edge: Narrow, close to 187A. Basal notch: Close to N186D. Leaf attachment point: Close to N186D. Midvein: Proximally, close to 147D; distally, close to 147C; midvein surrounded by close to N155D. Lateral venation: Close to 148B and 148C and surrounded by close to N155D; smaller veins, close to 138A. Interveinal areas: Close to 147D. Fully developed leaves, upper surface: Background color: Close to 192D and 155A. Towards the margins: Close to 137A, 137B to 137C, 194C and 194D. Leaf edge: Narrow, close to 187A to 187B. Basal notch: Close to 187A and 187C to 187D. Leaf attachment point: Typically, close to 187A and 187C. Midvein: Proximally, close to 193A with flecks, close to 139A; distally, close to 192A with flecks, close to 139A; midvein surrounded by close to NN155D. Lateral venation: Close to 139A and 194C and surrounded by close to NN155D; smaller veins, close to 138C and 139A. Interveinal areas: Close to 192D and N155A. Fully developed leaves, lower surface: Background color: Close to 147D, NN155C and NN155D. Towards the margins: Close to 191A, 191B and 138A. Leaf edge: Narrow, close to 187A and 187B. Basal notch: Close to 187B to 187C. Leaf attachment point: Close to 187B to 187C. Midvein: Proximally, close to 193A; distally, close to 194A; midvein surrounded by close to NN155D. Lateral venation: Proximally, close to 193A, 194C and 138A; distally, close to 139C; venation surrounded by close to N155D; smaller veins, close to 138D and 139C. Interveinal areas: Close to 147D, N155D, NN155C and NN155D.

*Petioles*.—Aspect: Initially upright and straight and leaning outwardly with development; flexible. Length, shade house-grown potted plants: About 20.5 cm to 34 cm. Diameter, distally, shade house-grown potted plants: About 3.3 mm to 5 mm. Diameter, proximally, shade house-grown potted plants: About 6 mm to 9 mm. Texture and luster: Smooth, glabrous; glaucous. Color, shade house-grown potted plants: When developing and fully developed: Close to 177D, 147D and 182D with stippling and streaks of close to 200A to 200B; just below the leaf junction, close to 146B and 146C. Wing length, shade house-grown potted plants: About 6.1 cm to 8.5 cm. Wing diameter, shade house-grown potted plants: About 9 mm to 10 mm. Texture and luster, inner and outer surfaces: Smooth, glabrous; dull. Wing color, shade house-grown potted plants: Outer surface: Close to 156B and 156C with stippling and streaks of close to 147A and 200B. Inner surface: Close to N155B; colors and patterns on the outer surface are visible on the inner surface.

Inflorescence description: Inflorescences observed on six week-old shade house-grown potted plants.

*Inflorescence arrangement*.—Upright hooded spathes surrounding a columnar spadix borne on an upright scape; spadix with sessile, simple female and male flowers separated into two zones; female flowers develop on the proximal one-third of the spadix; male flowers develop on the distal two-thirds of the spadix; sterile flowers develop at junction of female and male flower zones; near this junction, the spathe constricts and surrounds and encloses the female flowers; spathe open and cupped around male flowers.

*Fragrance*.—Night-fragrant; jasmine-like with camphor note.

*Natural flowering season and flower longevity*.—Plants of the new *Caladium* typically flower during the spring and summer in central Florida; flowers develop about six weeks after growth commences; inflorescences last about three days before fading; inflorescences persistent.

*Spathe*.—Length, overall: About 11.5 cm. Length, distal open portion: About 8 cm. Length, proximal closed portion: About 3.5 cm. Width, distal open portion: About 4.4 cm. Depth, distal open portion: About 2.7 cm. Width, at constriction: About 1.5 cm. Width, proximal closed portion: About 2.3 cm. Shape, open portion: Elliptic, slightly obovate. Apex: Acuminate. Base: Acute. Margin: Entire; smooth; open portion, reflexed. Texture and luster, front surface: Smooth, glabrous; dull. Texture and luster, rear surface: Smooth, glabrous; dull, proximally, glaucous. Color, front surface: Distal open portion: Close to 155C; with development, color becoming closer to 200C. Proximal closed portion: Close to 148C; towards the base, faintly tinged with close to N186C; color does not change with development. Color, rear surface: Distal open portion: Close to 145D and 155C; color does not change with development. Proximal closed portion: Close to 147B; color does not change with development.

*Spadix*.—Length, overall: About 8.4 cm. Length, male flower zone: About 6.4 cm. Length, sterile zone: About 1 cm. Length, female flower zone: About 2 cm. Diameter, male flower zone: About 1 cm. Diameter, sterile flower zone: About 7 mm. Diameter, female flower zone: About 1 cm. Shape: Columnar, spindle-shaped. Apex: Acute. Base: Obtuse. Aspect: Upright. Color, mature, male zone: Close to 158D. Color, mature, sterile zone: Close to 155C. Color, mature, female zone: Close to 159C. Male flowers: Quantity per spadix: About 225. Shape: Obovate. Height: About 3.5 mm. Diameter: About 3 mm. Pollen amount: Abundant. Pollen color: Close to 4D. Female flowers: Quantity per spadix: About 260. Shape: Obovate. Height: About 3 mm. Diameter: About 2 mm. Stigma color: Close to 159C. Ovary color: Close to 159C.

*Scape*.—Length: About 21 cm. Diameter: About 5 mm. Strength: Sturdy; flexible. Aspect: Mostly erect. Texture and luster: Smooth, glabrous; dull sheen; distally, slightly glaucous. Color: Close to 147B with stippling, streaks and tessellations of close to N199A.

*Seeds and fruits*.—To date, seed and fruit development have not been observed on plants of the new *Caladium*.

Pathogen & pest tolerance: Plants of the new *Caladium* have been observed to have average tolerance to *Pythium* Root Rot and above average tolerance to *Xanthomonas* Leaf Spot. Plants of the new *Caladium* have not been observed to have resistance to pests and other pathogens common to *Caladium* plants.

Temperature tolerance: Plants of the new *Caladium* have been observed to be tolerant to temperatures ranging from about 7° C. to about 40° C. and are suitable for USDA Hardiness Zones 8A to 11. In cooler zones, tubers can be "lifted" prior to first freeze and stored in a cool dry environment to overwinter for re-planting the following spring.

It is claimed:

1. A new and distinct *Caladium* plant named 'MOL 158-47' as illustrated and described.

* * * * *